United States Patent [19]
Dhaliwal

[11] Patent Number: 5,886,029
[45] Date of Patent: Mar. 23, 1999

[54] METHOD AND COMPOSITION FOR TREATMENT OF DIABETES

[76] Inventor: Kirpal S. Dhaliwal, 6181 Eastern Ave., Bell Gardens, Calif. 90201

[21] Appl. No.: 924,512

[22] Filed: Sep. 5, 1997

[51] Int. Cl.$^6$ .......................... A61K 31/35; A61K 35/78
[52] U.S. Cl. ...................... 514/456; 514/866; 424/195.1
[58] Field of Search ..................... 424/195.1; 514/866, 514/456

[56] References Cited

U.S. PATENT DOCUMENTS

| | | | |
|---|---|---|---|
| 5,318,986 | 6/1994 | Hara et al. | 514/456 |
| 5,730,988 | 3/1998 | Womack | 424/195.1 |

OTHER PUBLICATIONS

Seema et al., Chemical Abstract 125:218687 (1996).
Cha Hopadhyay, Chemical Abstracts 1996:301053.
Basnet et al., Chemical Abstracts 124:193946 (1995).
Functional Beta Cell Regeneration in the Islets of Pancreas in Alloxan Induced Diabetic Rats by (−)–Epicatechin by B.K. Chakravarthy, Saroj Gupte, and K. D. Gode Life Sciences, vol. 31, pp. 2693–2697 (1982).
Studies on Protein–Bound Polysaccharide Components & Glycosaminoglycans in Experimental Diabetes—Effect on Gymnema Sylvestre R.Br. Asha N. Baimi et al Indian Journal of Experimental Biology, vol. 19, Aug. 1981, pp. 715–721.
Effect of Trigonella Foenum Graecum (Fenugreek) on Blood Glucose in Norman and Diabetic Rats P. Khosla et al Indian Journal of Physiol Pharmacol, 1995: 39(2); 173–174.

*Primary Examiner*—Kevin E. Weddington
*Attorney, Agent, or Firm*—Charles H. Thomas

[57] ABSTRACT

A medicinal composition is provided for treatment of diabetes in a human subject. The medicinal composition of the invention induces a significant reduction in serum glucose due to the regeneration of pancreatic islet cells. A medicinal composition according to the invention necessarily includes a pharmacologically significant quantity of (−)epicatechin augmented with a comparable amount of gymnemic acid. For best results smaller quantities of *cinnamomum tamala, syzygium cumini, trigonella foenum graceum, azardichta indica, ficus racemosa*, and *tinospora cordifolia* are also included in the composition. One to two grams of the medicinal composition of the invention are administered to a diabetic human subject three times a day before meals. The unique combination of components in the medicinal composition leads to a regeneration of the pancreas cells which then start producing insulin on their own. Since the composition restores normal pancreatic function, treatment can be discontinued after between about four and twelve months.

20 Claims, No Drawings

METHOD AND COMPOSITION FOR TREATMENT OF DIABETES

BACKGROUND OF THE INVENTION

1. Field of the Invention

The present invention relates to a medicinal composition useful for the treatment of diabetes in a human patient, and a method of treating a human patient for diabetes.

2. Description of the Prior Art

It is well known that diabetes is a very serious, chronic, medical condition that develops in a significant number of human beings. The onset of diabetes can occur in a human being at an early age, although many times a person will not develop a diabetic condition until much later in life. In any event, the condition of diabetes is quite debilitating unless treated, and often leads to complications in other medical conditions that a patient may have. Diabetes often advances the onset of medical conditions and ailments associated with aging and very often leads to complications in treating such conditions.

The medical condition of diabetes is characterized by the inability of the pancreas gland to secrete insulin. Insulin is important to the human system because it enters the blood stream and helps the body burn sugar in the cells of the body in order to provide energy. In a diabetic patient sugar is not properly metabolized to produce energy. As a result, diabetic patients experience an elevated level of sugar in the blood.

The pancreas gland in the normal human system has a sufficient number of cells called beta cells that produce an adequate amount of insulin in the human body to properly metabolize sugar in a person's system. In a person who has developed diabetes, however, the pancreas deteriorates and the beta cells in the pancreas are too small and insufficiently numerous to produce a proper amount of insulin. As a consequence, the conventional treatment of diabetes involves the administration of insulin to a patient, typically by means of injections. These injections must be performed on a very regular basis and are normally administered using a hypodermic needle. This is inconvenient to a patient, since the administration of insulin using a hypodermic needle requires both a suitable place and time to perform the injection. Also, if the amount of insulin injection is excessive for the amount of sugar in the blood, the patient can undergo insulin shock. This condition is not only frightening to other persons in the vicinity, but is also quite dangerous for the patient.

Furthermore, the administration of insulin never really cures diabetes. To the contrary, a person suffering from diabetes must continue taking insulin injections for life. Moreover, it is well documented that diabetes tends to shorten a person's life span.

SUMMARY OF THE INVENTION

It has been discovered according to the present invention that a combination of certain products derived from plants can be utilized successfully in the treatment of diabetes and indeed cure that condition in at least some patients. These plant products possess hypoglycemic activity. That is these products have demonstrated the ability to decrease the level of sugar in the blood. More specifically, the combination of these products decreases serum glucose by increasing beta cell regeneration in the pancreas.

A number of the components employed in the composition of the invention have been documented as exhibiting hypoglycemic activity in test subjects. However, such activity has heretofore continued only as long as the administration of the substances involved continues. When the administration of these substances is halted, the pancreas of the subject ceases to produce the proper amount of insulin.

While a preferred medicinal composition according to the present invention utilizes a combination of several components that enhance beta cell regeneration, the most important of these are (−)epicatechin and gymnemic acid. (−)Epicatechin acts in the body to regenerate the beta cells of islets of the pancreas. With the administration of (−)epicatechin in combination with gymnemic acid on a regular basis, the beta cells of a diabetic subject will grow back to approach the normal size and number present in a nondiabetic person. This effect upon the body reverses the condition of diabetes. As the subject's blood sugar level improves, the dosage administered is reduced in strength. In at least some cases further administration has been discontinued entirely and the subject continues to produce a normal amount of insulin without further treatment. The subject is thereby not only treated but cured entirely of a diabetic condition.

In one broad aspect the present invention may be considered to be a medicinal composition comprising between about 0.5 grams and 2.0 grams of (−)epicatechin and between about 0.5 grams and 2.0 grams of gymnemic acid.

(−)Epicatechin is a chemical substance found in pterocarpus marsupium. Preferably a medicinal composition containing between 0.5 grams and 2.0 grams of (−)epicatechin is administered to a human subject three times during each twenty-four-hour period.

While (−)epicatechin is the primary and most essential beneficial component of the medicinal composition of the invention, this composition includes other components as well. Specifically, the medicinal composition of the invention is further comprised of gymnemic acid.

Gymnemic acid is present in a different plant substance, such as the leaves of *gymnema sylvestre*. When incorporated into the composition of the invention, gymnemic acid suppresses the taste buds in the oral cavity of the subject so that the individual does not taste the sweetness of sugar in food products consumed. This serves to reduce the craving for sugar in the human subject to which the medicinal composition has been administered. Gymnemic acid is made up of molecules whose atom arrangement is similar to those of glucose molecules. These molecules fill the receptor locations on the taste buds for a period of one to two hours, thereby preventing the taste buds from being activated by any sugar molecules present in the food. The desire to eat foods containing sugar is thereby suppressed.

Gymnemic acid also acts upon the absorptive surfaces of the stomach and intestine to retard absorption of sugar in foods that have been eaten. The glucose molecules in the gymnemic acid also fill the receptor locations in the absorptive, external layers of the intestine, thereby preventing the intestine from absorbing sugar molecules.

Other components are also preferably incorporated into the medicinal composition of the invention. The preferred embodiments of the medicinal composition of the invention include between 0.5 grams and about 5.0 grams of the leaves of *cinnamomum tamala*. This substance is an herb that aids in the digestion of food.

The medicinal composition of the invention also preferably includes between 0.5 grams and 6.0 grams of seeds of *momardica chirantia*. This herb aids in reducing the level of sugar in the blood.

The medicinal composition of the invention also preferably includes between 0.5 grams and 6.0 grams of the fruit of *syzygium cumini*. *Syzygium cumini* acts as a stimulant to the beta cells of Langerhans islets of the pancreas to secrete more insulin. Also, *syzygium cumini* increases the utilization of sugar either by direct stimulation of sugar uptake or through the mediation of enhanced insulin secretion.

Further components are also preferably incorporated into the medicinal composition of the invention. Specifically, the novel medicinal composition preferably also includes between 0.5 grams and about 5.0 grams of the seeds of *trigonella foenum graceum*. This is an herbal substance that delays the intestinal absorption of glucose. Between 0.5 grams and 5.0 grams of leaves of *azadirachta indica* are also preferably incorporated into the composition. *Azadirachta indica* has been observed to have hypoglycemic and antihypoglycemic effects.

Two other herbal substances are also preferably included in the preferred formulation of the medicinal composition of the invention. Between 0.5 grams and 5.0 grams of the leaves of *ficus racemosa* are preferably included in the composition. This is an herbal substance that has been reported to have antihyperglycemic activity. Also, between 0.5 grams and 5.0 grams of stems of *tinospora cordifolia* are also included in the preferred formulation of the invention. This herbal substance has been shown to increase glucose tolerance in diabetic rats.

In another broad aspect the present invention may be considered to be a medicinal composition comprising between about 0.5 grams and about 5.0 grams of *pterocarpus marsupium* and between about 0.5 grams and 5.0 grams *gymnema sylvestre*.

The heartwood of the herb *pterocarpus marsupium* may be crushed into a coarse power and administered in a raw form in an amount of between 1.0 grams and 5.0 grams three times a day. Preferably, however, it is administered in an extract form in an amount of between about 0.5 grams and 3.0 grams three times per day.

The leaves of the plant *gymnema sylvestre* are also ground into a powder. If incorporated into the medicinal composition in raw form, an amount of between about 1.0 grams and 5.0 grams of *gymnema sylvestre* are preferably included in the composition, which is administered three times daily. If employed in an extract form, preferably between about 0.5 grams and 3.0 grams of *gymnema sylvestre* are incorporated into the composition. Alternatively, gymnemic acid may be isolated from the *gymnema sylvestre* leaves, in which case between about 0.5 grams and 2.0 grams of gymnemic acid are utilized in the composition.

Likewise *cinnamomum tamala* may be administered in either raw or extract form. If administered in raw form, preferably between about 1.0 grams and 5.0 grams are utilized in the composition. If present in extract form, preferably between about 0.5 grams and 2.0 grams of *cinnamomum tamala* are utilized.

The remaining components may likewise be utilized in either raw or extract form. If employed in a raw form, preferably between about 1.0 grams and 6.0 grams of *syzygium cumini* are utilized. Alternatively, an extract of *syzygium cumini* of between about 0.5 grams and 3.0 grams may be utilized in the composition. When raw *trigonella foenum graceum* is utilized, it preferably present in the composition in an amount of between about 1.0 grams and 5.0 grams. If present in an extract form, preferably between about 0.5 grams and 3.0 grams of *trigonella foenum graceum* are used in the composition.

When *aegle marelose* and *momardica chirantia* are included in the medicinal composition of the invention, preferably between about 0.5 grams and 6.0 grams of either or both of these substances are utilized. Alternatively, extracts in an amount of between about 0.5 grams and about 3.0 grams of either or both substances are included.

Between 1.0 grams and 5.0 grams of raw *azadirachta indica* may be employed in the composition. Alternatively, an extract of this herbal substance in an amount of between about 0.5 grams and 3.0 grams may be employed instead.

When *ficus racemosa* is employed in a raw form, between about 0.5 grams and 5.0 grams of this herbal substance are preferably incorporated into the medicinal composition. When utilized in extract form, the medicinal composition preferably includes between about 0.5 grams and 2.5 grams of *ficus racemosa*.

When *tinospora cordifolia* is employed in the composition, between about 0.5 grams and 5.0 grams of this raw herbal substance may be utilized. Alternatively, an extract of *tinospora cordifolia* in an amount of between about 0.5 grams and 3.0 grams may be employed in the composition.

It is to be understood that greater or lessor amounts of each component may be utilized in the composition of the invention. The suggested formulations previously given herein are appropriate for administration to human subjects of dosages pressed into pills or capsules three times a day. Pills or capsules formulated with smaller amounts of each of these components may likewise be employed, but would have to be administered more frequently. The use of smaller, more frequent dosages has the advantages of providing a more uniform quantity of the active ingredients to the systems of the subjects, but is disadvantageous due to the high frequency of administration required.

Conversely, dosages employing greater amounts of these components in a medicinal composition according to the invention may be utilized, and administered less frequently. However, the level of the active substances in the system of the patient will vary more if the composition is administered less frequently. The dosages containing the quantities of components previously suggested herein are considered to be optimum for a human subject of typical body weight.

To produce the composition of the invention in its preferred form, each of the component plant products were crushed into a coarse powder which was then mixed with water at a ratio of one to eight, weight to volume. The components were soaked separately for twenty-four hours. The soaked material with water was then boiled until it was reduced to one-quarter of its initial volume and then filtered through a muslin cloth filter. The resultant extracts were then made into a semisolid by the application of low heat. The extracts thus obtained were air dried at room temperature and made into a powder. These powders were then mixed in the relative amounts set forth in Table 1 below, all percentages being expressed by dry weight.

TABLE 1

| Substance | Percentage |
| --- | --- |
| pterocarpus marsupium | 30.0 |
| (heartwood containing (-)epicatechin) | |
| gymnema sylvestre | 27.0 |
| (leaves containing gymnemic acid) | |
| cinnamomum tamala (leaves) | 3.0 |
| aegle marelose (leaves) | 6.0 |
| momardica chirantia (seeds) | 6.0 |
| azadirachta indica (leaves) | 3.0 |
| tinospora cordifolia (stem) | 5.0 |
| trigonella foenum graceum (seeds) | 10.0 |
| ficus racemosa (leaves) | 2.0 |
| syzygium cumini (fruit) | 8.0 |

The foregoing composition may be described as a Pancreas Tonic.

Another broad aspect of the invention resides in the use of the composition according to the invention. Specifically, this aspect of the invention may be considered a method for treating diabetes in a human patient comprising administering to the patient between about 0.5 grams and about 2.0 grams (-)epicatechin and between about 0.5 grams and 2.0 grams of gymnemic acid at least once a day, and preferably three times over a twenty-four-hour period. In a preferred manner of implementation, each administration of (−)epicatechin and gymnemic acid is accompanied by the administration of between 0.5 grams and 5.0 grams of each of the following substances: *cinnamomum tamala, syzygium cumini, trigonella foenum graceum, aegle marelose, momardica chirantia, azadirachta indica, ficus racemosa,* and *tinospora cordifolia.*

The efficacy of the Pancreas Tonic according to the invention was first demonstrated by animal tests. Specifically, thirty Sprague-Dawley male rats six weeks of age were evenly divided into three groups of ten each. These animals were randomly assigned to the following groups: (A) Control Group; (B) Diabetic Group; and (C) Pancreas Tonic Diet Group.

The rats of Control Group A were placed on normal rat chow and subjected to no further treatment. The rats of Diabetic Group B were each given an intraperitoneal injection of Alloxan (80 milligrams/kilogram body weight) after four to six hours of food withdrawal and thereafter placed on normal rat chow. The rats of Pancreas Tonic Diet Group C were also each given an intraperitoneal injection of Alloxan (80 milligrams/kilogram body weight) after four to six hours of food withdrawal and placed on a diet of normal rat chow supplemented with two percent weight/weight of the Pancreas Tonic formulated as set forth in Table 1.

All of the animals were placed on their respective diets for a period of twelve weeks. Body weights and feed consumption were recorded weekly. All animals were observed daily for general growth and normal movements in their cages. No significant changes were observed in the overall health of these animals during the period of study.

At the end of the study period, blood samples were collected and processed from each animal. Access to the food supplies was then withdrawn for approximately four hours and the animals were anesthetized by ketamine-xylazine (eighty milligram-eight milligram/kilogram intraperitoneal injection) and blood samples were collected by ten milliliter syringes with eighteen gauge needles. Approximately eight to ten milliliters of blood from each animal were placed in tubes for serum and three to four milliliters were placed in lavender top tubes for glycosylated hemoglobin analysis.

Serum biochemistry analyses were then performed. All samples were coded with numbers and the technician who performed the analysis was blinded from seeing the group information. Serum samples were analyzed for chem.-20 panel using a standard Beckman Synchron CX-7 autoanalyzer. Glycosylated hemoglobin concentrations were determined by a routine gel electrophoretic method using a DiaSTAT system made by BioRAD of San Francisco, Calif.

Histological slides were then prepared. The pancreas was excised from each of the euthanized rats and fixed in ten percent buffered formalin. Paraffin blocks were prepared and five microsections were cut with a "820" Spencer microtome manufactured by American Optical Corporation. Routine microscopic slides were prepared. Hematoxylin—Eosin staining was performed and all slides were histologically examined for number of islets and total number of cells per pancreatic islet.

A statistical Analysis was then performed. All observations were first recorded in a note book and entered into a Macintosh LCII computer. Data was verified by a second person for accuracy of data entry. The statistical analysis was performed using a StatView 4.5 software program manufactured by Abacus Concepts. The significance of differences among groups were determined by ANOVA and Fisher's PLSD test with P values.

The body weights of the rats in the three groups were tabulated and it was determined that the final body weights of all three groups had uniformly increased, but without any significant differences among the groups. The serum glucose and glycosylated hemoglobin (GHB) values were then tabulated. The results of this tabulation are set forth in Table 2.

TABLE 2

Effect of Pancreas Tonic-treatment on the serum glucose and glycosylated hemoglobin in experimental rats.

| Groups | Serum glucose (mg) | Glycosylated hemoglobin (%) |
|---|---|---|
| Control Group A rats | 133 ± 12.3 | 8.1 ± 0.27 |
| Diabetic Group B rats | 182 ± 16.4* | 9.1 ± 0.23* |
| Pancreas Tonic Diet Group C rats | 95 ± 8.9** | 7.0 ± 0.29** |

*significantly higher compared to control group (P < 0.01)
**significantly lower compared to diabetic group (P < 0.0001)

The serum glucose concentration in Control Group (A) was 133 mg±12.3; Diabetic Group (B): 182 mg±16.4; Pancreas Tonic Diet Group (C): 95 mg±8.9. It was observed that the Diabetic Group (B) had significantly higher serum glucose levels compared to the levels found in the Control Group (A). The Pancreas Tonic Diet Group (C) had significantly lower serum glucose concentration levels compared to Diabetic Group (B). The percentage of glycosylated hemoglobin in Control Group (A) was: 8.1±0.27; Diabetic Group (B): 9.1±0.23; and Pancreas Tonic diet group (c): 7.0±0.29. The Diabetic Group (B) GHB was significantly higher compared to the Control Group (A). The Pancreas Tonic Diet Group (C) had a significantly lowered GHB compared to the Diabetic Group (B) and the Control Group (A).

The histological analysis of pancreas of the rats showed a generalized reduction in size and number of islets in Diabetic Group (B) and regeneration of islets in Pancreas Tonic Diet Group (C) compared to the Diabetic Group (B). The total number of cells per islet were counted. The number of cells per islet are presented in Table 3.

TABLE 3

Effect of Pancreas Tonic-treatment on the number of cells per pancreatic islet in experimental rats.

| Groups | Number of Cells per Pancreatic Islet |
|---|---|
| Control Group A rats | 111 ± 8.9 |
| Diabetic Group B rats | 40 ± 14* |
| Pancreas Tonic Diet Group C rats | 79 ± 8.8** |

*significantly lower compared to Control Group (A) (P < 0.02)
**significantly higher compared to Diabetic Group (B) (P < 0.02)

It was observed that the Diabetic Group (B) had a significant reduction in number of beta cells compared to Control Group (A). The Pancreas Tonic Diet Group (C) contained significantly more beta cells compared to Diabetic Group (B).

The serum glucose data obtained suggests that intraperitoneal alloxan injections did elevate the glucose concentration as is evident from Table 2. Information on the glycosylated hemoglobin (GHB) levels supports the fact that the glucose elevations in serum were chronic in the Diabetic Group (B) of rats. On the other hand, the Pancreas Tonic treatment significantly decreased the serum glucose concentration with a significant reduction in GHB in the Pancreas Tonic Diet Group (C). This demonstrates not only a hypoglycemic effect of the Pancreas Tonic of Table 1, but also a reduction in GHB.

The histological evidence provided in the rat study described herein demonstrated that alloxan injections destroyed the pancreatic beta cells in the Diabetic Group (B) of rats. A very significant reduction in total number of cells per pancreatic islet were observed in this group with a generalized shrinkage in size of islets. This observation supported the fact that an increase in serum glucose of diabetic rats was due to the damage done to pancreatic islets.

The Pancreas Tonic Diet Group (C) had a significantly higher number of cells per pancreatic islet than was observed in the Diabetic Group (B). This suggests that the Pancreas Tonic treatment substance of Table 1 regenerated the pancreatic islet cells. The histological observation of regeneration of islet cells in the Pancreas Tonic Diet Group (C) correlates with a significant reduction of serum glucose and GHB at systemic level.

Extrapolating from the relative weights of the rats in the test group comparable dosages of the Pancreas Tonic of Table 1 were administered to each human subject in a group of thirty diabetic human subjects. Specifically, the thirty human subjects in the test group, each suffering from diabetes, were each orally administered pills having an aggregate weight of about 7.0 grams and formulated according to the Pancreas Tonic of Table 1. The pills were administered three times a day before meals. It was observed that after only about four to six months of this regimen the diabetic conditions of all the subjects significantly improved, and became at least partially reversed.

After between six and twelve months, administration of the Pancreas Tonic of Table 1 to five of the test subjects whose blood sugar levels had reached normal levels was terminated entirely. Nevertheless, all of these individuals continued to maintain normal blood sugar levels and exhibited no other signs of diabetes. After this same time, only one-half of one pill of the Pancreas Tonic of Table 1 was administered to each remaining subject in the test group three times a day, and their blood sugar levels have remained normal. Accordingly, it is evident that the medicinal composition of the invention, and the treatment of the human subjects with this composition, has exhibited a remarkably beneficial effect. In same cases the subjects appear to be totally cured, while in other cases the improvement is dramatic, if not yet total.

Undoubtedly, numerous other variations and modifications of the invention will become readily apparent to those familiar with the formulation of medicinal compositions. For example, the relative concentrations of the components of the Pancreas Tonic may be varied significantly from those set forth in Table 1 while still providing a considerable benefit to the subject. Also, the composition of the invention may be augmented with other substances that show a hypoglycemic effect, and such other substances may be substituted for one or more of the components of the Pancreas Tonic formulated as set forth in Table 1. Also, the medicinal composition of the invention may be pressed into capsules and incorporated into other conventional types of medication delivery systems besides pills.

Accordingly, the scope of the invention should not be construed as limited to the specific suggested formulation of the medicinal composition as set forth herein, nor to the suggested dosages or manner of administration. Such variations and modifications are well within the level of skill of one familiar with the disease of diabetes.

I claim:

1. A medicinal composition comprising between about 0.5 grams and about 2.0 grams of (−)epicatechin and between about 0.5 and about 2.0 grams of gymnemic acid.

2. A medicinal composition according to claim 1 further comprising between about 0.5 and about 5.0 grams of *cinnamomum tamala*.

3. A medicinal composition according to claim 1 further comprising between about 0.5 and 6.0 grams of *syzygium cumini*.

4. A medicinal composition according to claim 1 further comprising between about 0.5 and about 5.0 grams *trigonella foenum graceum*.

5. A medicinal composition according to claim 1 further comprising between about 0.5 and about 5.0 grams *azardichta indicia*.

6. A medicinal composition according to claim 1 further comprising between about 0.5 and about 5.0 grams of *ficus racemosa*.

7. A medicinal composition according to claim 1 further comprising between about 0.5 and about 5.0 grams of *tinospora cordifolia*.

8. A medicinal composition according to claim 1 further comprising between about 0.5 and about 6.0 grams of *aegle marelose*.

9. A medicinal composition according to claim 1 further comprising between about 0.5 and about 6.0 grams of *momardica chirantia*.

10. A medicinal composition comprising between about 0.5 and about 5.0 grams of *pterocarpus marsupium* and between about 0.5 and about 5.0 grams *gymnema sylvestre*.

11. A medicinal composition according to claim 10 wherein said *pterocarpus marsupium* is in extract form and is present in an amount of between about 0.5 and about 3.0 grams.

12. A medicinal composition according to claim 11 wherein said *gymnema sylvestre* is in extract form and is present in an amount of between about 0.5 and 3.0 grams.

13. A medicinal composition according to claim 12 further comprising between about 0.5 and about 5.0 grams *cinnamomum tamala*, between about 0.5 and about 6.0 grams *syzygium cumini*, between about 0.5 and about 5.0 grams *trigonella foenum graceum*, between about 0.5 and about 5.0 grams *azadirachta indica*, between about 0.5 and 5.0 grams *ficus racemosa*, between about 0.5 and about 6.0 grams *aegle marelose*, between about 0.5 and about 6.0 grams *momardica chirantia*, and between about 0.5 and 5.0 grams *tinospora cordifolia*.

14. A medicinal composition according to claim 13 wherein said *pterocarpus marsupium*, said *gymnema sylvestre*, said *cinnamomum tamala*, said *syzygium cumini*, said *trigonella foenum graceum*, said *azadirachta indica*, said *aegle marelose*, said *momardica chirantia*, said *ficus racemosa* and said *tinospora cordifolia* are all present as extracts, each in a quantity no greater than about 3.0 grams.

15. A method of treating diabetes in a human patient comprising administering to said patient between about 0.5 grams and about 2.0 grams (−)epicatechin and between about 0.5 and about 2.0 grams of gymnemic acid at least once a day.

16. A method according to claim 15 further comprising administering said (−)epicatechin and gymnemic acid as aforesaid at least three times over a twenty-four-hour period.

17. A method according to claim 16 further comprising terminating said administration after a period of no more than twelve months.

18. A method according to claim 15 further comprising administering with each administration of (−)epicatechin and gymnemic acid between about 0.5 and 5.0 grams of each of the following substances: *cinnamomum tamala, syzygium cumini, trigonella foenum graceum, aegle marelose, momardica chirantia, azadirachta indicia, ficus racemosa,* and *tinospora cordifolia*.

19. A method according to claim 15 further comprising deriving said gymnemic acid as an extract of *gymnema sylvestre*.

20. A method according to claim 15 further comprising deriving said (−)epicatechin as an extract of *pterocarpus marsupium*.

* * * * *